United States Patent
Zeng et al.

(10) Patent No.: US 12,135,333 B2
(45) Date of Patent: Nov. 5, 2024

(54) DETECTION KIT FOR DETECTING IMMUNOSUPPRESSORS IN WHOLE BLOOD BY HIGH PERFORMANCE LIQUID CHROMATOGRAPHY-TANDEM MASS SPECTROMETRY AND DETECTION METHOD THEREOF

(71) Applicant: Hangzhou Calibra Diagnostics Co., Ltd., Zhejiang (CN)

(72) Inventors: Shanshan Zeng, Hangzhou (CN); Qi Zhang, Hangzhou (CN); Baoyu Han, Hangzhou (CN); Huafen Liu, Hangzhou (CN)

(73) Assignee: HANGZHOU CALIBRA DIAGNOSTICS CO., LTD., Hangzhou (CN)

( * ) Notice: Subject to any disclaimer, the term of this patent is extended or adjusted under 35 U.S.C. 154(b) by 452 days.

(21) Appl. No.: 17/511,861

(22) Filed: Oct. 27, 2021

(65) Prior Publication Data

US 2022/0404380 A1  Dec. 22, 2022

Related U.S. Application Data

(63) Continuation of application No. 17/460,739, filed on Aug. 30, 2021, now abandoned.

(30) Foreign Application Priority Data

Jun. 17, 2021 (CN) .......................... 202110673324.1

(51) Int. Cl.
| | | |
|---|---|---|
| *G01N 33/96* | (2006.01) | |
| *G01N 1/28* | (2006.01) | |
| *G01N 1/38* | (2006.01) | |
| *G01N 30/02* | (2006.01) | |
| *G01N 30/04* | (2006.01) | |
| *G01N 30/06* | (2006.01) | |
| *G01N 30/34* | (2006.01) | |
| *G01N 30/72* | (2006.01) | |
| *G01N 30/88* | (2006.01) | |
| *G01N 33/68* | (2006.01) | |
| *G01N 33/94* | (2006.01) | |

(52) U.S. Cl.
CPC ............. *G01N 33/96* (2013.01); *G01N 1/286* (2013.01); *G01N 1/38* (2013.01); *G01N 30/06* (2013.01); *G01N 30/34* (2013.01); *G01N 30/7233* (2013.01); *G01N 33/9493* (2013.01); *G01N 2030/027* (2013.01); *G01N 2030/045* (2013.01); *G01N 2030/8822* (2013.01); *G01N 2030/8831* (2013.01); *G01N 33/6848* (2013.01)

(58) Field of Classification Search
CPC .... G01N 1/286; G01N 1/38; G01N 2030/027; G01N 2030/045; G01N 2030/8822; G01N 2030/8831; G01N 2496/00; G01N 30/02; G01N 30/04; G01N 30/06; G01N 30/34; G01N 30/72; G01N 30/7233; G01N 30/88; G01N 33/6848; G01N 33/82; G01N 33/9493; G01N 33/96
See application file for complete search history.

(56) References Cited

U.S. PATENT DOCUMENTS

| | | | | |
|---|---|---|---|---|
| 2017/0138940 | A1* | 5/2017 | Goethel | ................. B01D 15/02 |
| 2020/0003666 | A1* | 1/2020 | Lopez-Calle | ........ G01N 33/743 |

FOREIGN PATENT DOCUMENTS

| | | | | | |
|---|---|---|---|---|---|
| CN | 110470753 | A | * | 11/2019 | ............. G02N 30/06 |
| CN | 110554123 | A | * | 12/2019 | ............. G01N 30/06 |
| CN | 111679023 | A | * | 9/2020 | ............. G01N 30/06 |
| CN | 111693635 | A | * | 9/2020 | ............. G01N 30/06 |
| CN | 112710766 | A | * | 4/2021 | ............. G01N 30/06 |
| CN | 112924606 | A | * | 6/2021 | ............. G01N 30/06 |

OTHER PUBLICATIONS

Gong et al, A high-throughput LC-MS/MS method for the quantification of four immunosuppressants drugs in whole blood, Clinica Chimica Acta 498 (2019) 21-26 (Year: 2019).*
Ansermot et al, Simultaneous quantification of cyclosporine, tacrolimus, sirolimus and everolimus in whole blood by liquid chromatography-electrospray mass spectrometry, Clinical Biochemistry 41 (2008) 728-735 (Year: 2008).*
Rigo-Bonnin et al, Simultaneous Measurement of Cyclosporine A, Everolimus, Sirolimus and Tacrolimus Concentrations in Human Blood by UPLC-MS/MS, Chromatographia (2015) 78:1459-1474 (Year: 2015).*
Deters et al, Liquid chromatography/mass spectrometry for therapeutic drug monitoring of immunosuppressants, Analytica Chimica Acta 492 (2003) 133-145 (Year: 2003).*

(Continued)

*Primary Examiner* — David L Singer
(74) *Attorney, Agent, or Firm* — NZ CARR LAW OFFICE

(57) ABSTRACT

A detection kit for detecting an immunosuppressor in whole blood by high performance liquid chromatography-tandem mass spectrometry and a detection method thereof is provided. An internal standard solution is added with an antioxidant, vitamin E, and mixed with an internal standard diluent containing zinc sulfate heptahydrate, purified water and methanol for sample pretreatment, which not only exerts the function of the internal standard, but also synchronously achieves erythrocyte treatment, protein precipitation and target substance extraction. Various embodiments enable the immunosuppressor to be more stable in a solution matrix, thus promoting the detection accuracy and sensitivity. Various embodiments adopt isotopically-labeled sirolimus as an internal standard of everolimus to substitute isotopically-labeled everolimus, thus overcoming the interference of everolimus on isotopically-labeled everolimus and satisfying the detection requirements. Various embodiments detect four immunosuppressors simultaneously to reduce the cost of the internal standard, and has a lower detection cost, more accurate and stable detection results.

18 Claims, 4 Drawing Sheets

(56) References Cited

OTHER PUBLICATIONS

Tszyrsznic et al, Two rapid ultra performance liquid chromatography/tandem mass spectrometry (UPLC/MS/MS) methods with common sample pretreatment for therapeutic drug monitoring of immunosuppressants compared to immunoassay, Journal of Chromatography B, 928 (2013) 9-15 (Year: 2013).*

Hatsis et al, Evaluation of a cyano stationary phase for the determination of tacrolimus, sirolimus and cyclosporin A in whole blood by high-performance liquid chromatography-tandem mass spectrometry, Journal of Chromatography B, 809 (2004) 287-294 (Year: 2004).*

* cited by examiner

DETECTION KIT FOR DETECTING IMMUNOSUPPRESSORS IN WHOLE BLOOD BY HIGH PERFORMANCE LIQUID CHROMATOGRAPHY-TANDEM MASS SPECTROMETRY AND DETECTION METHOD THEREOF

CROSS-REFERENCE TO RELATED APPLICATION(S)

This application is a continuation of U.S. patent application Ser. No. 17/460,739 filed on Aug. 30, 2021, which claims priority to China patent application no. 2021106733241 filed on Jun. 17, 2021.

TECHNICAL FIELD

The present invention belongs to the technical field of biochemical analysis; and particularly relates to a detection kit for detecting an immunosuppressor in whole blood by high performance liquid chromatography-tandem mass spectrometry and a detection method thereof.

BACKGROUND

Immunosuppressor is a kind of medicaments capable of inhibiting body's abnormal response, and can inhibit the proliferation and function of immunoreaction-associated cells (T cell, B cell and other macrophages), thus reducing immune response. Immunosuppressor is mainly used for preventing the rejection reaction in organ transplantation and for the treatment of autoimmune diseases clinically, such as, rheumatic arthritis, lupus erythematosus, dermatomycosis, inflammatory bowel diseases, autoimmune hemolytic anemia. With the constant and better understanding to the rules of immune response, some novel high-efficient and low-toxicity immunosuppressors, such as, cyclosporine A, tacrolimus, sirolimus, and everolimus have been developed and applied. There are obvious intra-individual and interindividual differences in pharmacokinetics of immunosuppressors; moreover, the therapeutic concentration is close to the toxicity concentration, and slightly high blood concentration will lead to toxic and side effects, and slightly low blood concentration will lead to rejection reaction; therefore, the therapeutic window is very narrow. The efficacy and toxic and side effects of a medicament are closely associated with the dosage. Thereby, the medicament concentration in vivo can be monitored to reasonably guide the clinical adjustment of the dosage, thus ensuring that the medicament concentration is within a safe and effective therapeutic range.

Immunosuppressor can be used alone, or in combination use to enhance the therapeutic effect or alleviate the toxic and side effects of a medicament. From the aspect of mechanism of action, cyclosporine A and tacrolimus are calcineurin inhibitors to exert the immunosuppressive action mainly by inhibiting the activation of T cells. Cyclosporine A is a cyclic peptide composed of 11 amino acids, and has stronger lipophicity; about 50% of the cyclosporine A in blood are absorbed by erythrocyte, and 30% are bound on plasma lipoprotein and other proteins; and the blood concentration of cyclosporine A can be monitored by whole blood or plasma. Tacrolimus is a kind of macrolide compound separated from metabolites of *Streptomyces*; and its immunological competence is proved to be 50-100 times the cyclosporine A by in vitro experiments. Tacrolimus is mainly absorbed through a gastrointestinal tract, and the vast majority of tacrolimus are distributed in erythrocyte of blood, and the blood concentration of whole blood is clinically used to monitor and adjust the optimal dosage. Sirolimus and its derivative everolimus are triene macrolide compounds, and are sirolimus target protein inhibitors for mammal; after being administered, sirolimus and everolimus are widely distributed in each tissue, and mainly bound to erythrocyte in blood. Therefore, a whole blood sample is also clinically used for monitoring the medicament concentration.

Currently, there are lots of reports on the determination method of immunosuppressors in whole blood, and common methods include: immunoassay, and liquid chromatography; in numerous methods, liquid chromatography-tandem mass spectrometry is a preferred method to determine immunosuppressors. But there are many problems, such as, complicated operating process, more interference factors, poor specificity, long analysis time and low throughput in the conventional methods; it is mainly caused by complicated process and poor stability of the sample pretreatment.

The existing pretreatment method of the immunosuppressor sample mainly includes protein precipitation, liquid-liquid extraction and the like; for example, CN109187839A, zinc sulfate and methanol solution serve as a protein precipitant for pretreatment to a whole blood sample, thus detecting the four immunosuppressors in the sample, namely, tacrolimus, sirolimus, Everolimus and cyclosporine A. Due to poor stability in the sample pretreatment process, the detection result is interfered easily, error is large and detection sensitivity is low.

Therefore, it is in urgent need of a pretreatment method of an immunosuppressor sample having the advantages of simple operation, high treatment efficiency, high throughput, and high detection accuracy and sensitivity, low cost and small artificial workload, thereby overcoming the above shortcomings and defects in the existing method.

SUMMARY OF THE INVENTION

To solve the above problem, the present invention provides an improved detection kit for simultaneously detecting four immunosuppressors in whole blood by high performance liquid chromatography-tandem mass spectrometry and a detection method thereof. An internal standard solution is added with an antioxidant, vitamin E, and mixed with an internal standard diluent containing zinc sulfate heptahydrate, purified water and methanol for sample pretreatment. One step achieves erythrocyte treatment, protein precipitation and internal standard addition. Moreover, the present invention enables the immunosuppressors to be more stable in a solution matrix, thus promoting the detection accuracy and sensitivity. Meanwhile, the present invention also adopts isotopically-labeled sirolimus as an internal standard of everolimus to substitute isotopically-labeled everolimus, thus overcoming the interference of everolimus on isotopically-labeled everolimus and satisfying the detection requirements. Further, the present invention can reduce the cost of the internal standard, and has a lower detection cost, more accurate and stable detection results.

On the one hand, the prevent invention provides a detection kit for simultaneously detecting immunosuppressors in whole blood, and the detection kit comprises an internal standard solution, where the internal standard solution contains an additive, and the additive is any one or more of 2,6-di-tert-butyl-p-cresol, vitamin E, vitamin C, β-carotene, and sodium metabisulfite.

The immunosuppressors of the present invention include cyclosporine A, tacrolimus, sirolimus and everolimus.

Through a large number of experiments, the inventor proves that there is an obvious problem of poor stability of an immunosuppressor in a solution matrix, for example, an internal standard solution in a detection kit, the content of the immunosuppressor isotope internal standard contained therein is highly unstable, and will decline sharply after the internal standard solution is put for several days at room temperature, thereby significantly influencing the detection accuracy and sensitivity, such that all samples, standard samples, internal standards, quality control substances and the like used for detecting immunosuppressors need to be prepared when they are in need, which causes great troubles to the actual operation and brings a high detection cost. This is probably because immunosuppressor is a kind of macrolide compound; seen from the structure, the macrolide compound generally contains multiple double bonds intramolecularly, is prone to hydrolysis, and has a stronger chemical activity and poor stability in a solution matrix. Moreover, researches show that a triene group is easily oxidized to cause the degradation of sirolimus and everolimus. Therefore, to detect the content of four immunosuppressors in whole blood more accurately, it is very necessary to overcome the stability problem of immunosuppressors in a solution matrix first.

Surprisingly, the inventor finds that the addition of an antioxidant can significantly improve the stability of immunosuppressors, especially, the stability of sirolimus, everolimus and other trienemacrolide immunosuppressors.

Further, the additive is vitamin E.

Research shows that when the additive is vitamin E, the antioxidant effect is most obvious and the stabilizing effect is up to the optimal.

Further, the vitamin E has a concentration of 0.5-1.5 mg/mL.

Further, the vitamin E has a concentration of 1.0 mg/mL.

Further, the immunosuppressors are one or more of cyclosporine A, tacrolimus, sirolimus and everolimus.

Further, the internal standard solution further contains an immunosuppressor internal standard and acetonitrile, and the acetonitrile is a solvent of the internal standard solution.

Acetonitrile serves as a solvent of the internal standard solution to prevent the hydrolysis of macrolide immunosuppressors (tacrolimus, sirolimus an d everolimus), thus assisting the further improvement of stability.

Further, the immunosuppressor internal standard is an isotopically-labeled immunosuppressor, where an internal standard of cyclosporine A is isotopically-labeled cyclosporine A, an internal standard of tacrolimus is isotopically-labeled tacrolimus, and internal standards of sirolimus and everolimus are isotopically-labeled sirolimus.

A great number of research data show that everolimus disturbs the detection of internal standards by an everolimus isotope; therefore, the isotope internal standard of everolimus cannot be added to the internal standard directly. Sirolimus and everolimus have a very similar structure; therefore, the present invention adopts an isotope internal standard of sirolimus as an internal standard of everolimus, which can not only satisfy the detection requirements and reduce the cost of the internal standard, but also can further promote the accuracy and sensitivity of the detection result.

The internal standard solution containing vitamin E prepared by the present invention is very stable, and can be stored for a long time, and used at any time if necessary; and the service life is up to two years; therefore, the detection process is more simple and efficient, detection cost is lower, and the detection result is more accurate and stable.

Further, the detection kit further contains an internal standard diluent, and the internal standard diluent contains internal standard solution, purified water and methanol.

In this present invention, methanol, zinc sulfate heptahydrate, and purified water are prepared into an internal standard diluent, used for mixing with the internal standard directly, thus obtaining an internal standard working solution; then the internal standard working solution is added to a sample and mixed evenly, which not only exerts the effect of the internal standard, but also synchronously achieves the erythrocyte treatment, precipitation separation of protein and extraction of target substances in samples. Moreover, the solution system has good solubility to the immunosuppressor in samples; sample injection is performed for detection after separating impurities of the precipitate without freeze drying or liquid-liquid extraction, nitrogen purging and other enrichment process, thus simplifying the operating process. Moreover, the reagents used are low-cost conventional chemical reagents, reducing the detection cost.

Further, in the internal standard diluent, a volume ratio of purified water to methanol is 3:7, and zinc sulfate heptahydrate has a content of 60 mM.

Further, a volume ratio of the internal standard solution and the internal standard diluent is 1:24.

Further, the detection kit further contains a system suitability solution, wherein the system suitability solution comprises one or more of cyclosporine A, tacrolimus, sirolimus, and everolimus, as well as one or more of isotopically-labeled cyclosporine A, tacrolimus and sirolimus, and further comprises a solvent and an additive; the solvent is additive-containing acetonitrile; and the additive is any one or more of 2,6-di-tert-butyl-p-cresol, vitamin E, vitamin C, β-carotene, and sodium metabisulfite.

The system suitability solution is used for a system suitability test; before sample detection, the system suitability solution is directly fed for 3 times and detected by high performance liquid chromatography-tandem mass spectrometry to judge whether the high performance liquid chromatography-tandem mass spectrometry system is normal through the dwell time, response strength and precision of the target substance.

Acetonitrile serves as a solvent of the system suitability solution to prevent the hydrolysis of macrolide immunosuppressors (tacrolimus, sirolimus an d everolimus), thus assisting the further improvement of stability.

Further, the additive of the system suitability solution is vitamin E.

Further, the vitamin E has a concentration of 0.5-1.5 mg/mL.

Further, the vitamin E has a concentration of 1.0 mg/mL.

The system suitability solution containing vitamin E prepared by the present invention is very stable, and can be stored for a long time, and used at any time if necessary; therefore, the detection process is more simple and efficient, detection cost is lower, and the detection result is more accurate and stable.

Experimental results show that the internal standard solution and system suitability solution provided by the present invention can be stored for two years above at 2-8° C.

Further, the detection kit further includes standard samples and quality control samples; the standard samples and the quality control samples are prepared by using a sterile bovine blood containing a matrix additive as a matrix; the matrix additive comprises vitamin E; the standard sample is a sample comprising any one or more of cyclosporine A, tacrolimus, sirolimus and everolimus at a standard concentration; and the quality control sample is a sample comprising three different levels (low, medium and high) of concentrations.

Further, the vitamin E in the matrix additive has a concentration of 0.5-1.5 mg/mL.

Further, the preparation of the standard sample and quality control sample includes the following steps: using sterile bovine blood containing a matrix additive as a matrix; and adding a standard solution of any one or more of cyclosporine A, tacrolimus, sirolimus and everolimus; and preparing the immunosuppressor standard sample and quality control sample at series concentrations. The prepared standard sample and quality control sample can be lyophilized or kept in a form of liquid.

The sterile bovine blood is used to prepare the standard sample and quality control sample, which can not only provide a matrix environment simulating a whole blood sample of human, reduce matrix effects during sample detection, improve the accuracy and reliability of the standard curve and quality control sample, but also can reduce the production cost of the kit due to the accessibility of bovine blood.

In some examples, the matrix additive includes a preservative Proclin 300, an antioxidant vitamin E, a stabilizer tert-butyl alcohol, a solubilizer polyethylene glycol, an anticoagulant EDTA-2Na, an excipient bovine serum albumin, thus achieving anticorrosion, antioxidant, stabilizing, solubilizing, anticoagulant and form-giving effects.

Further, the detection kit further includes a mobile phase of liquid chromatography (LC); the mobile phase of LC comprises a mobile phase A and a mobile phase B; the mobile phase A is a 2 mM aqueous solution of ammonium acetate-0.1% formic acid; and the mobile phase B is 2 mM methanol solution of ammonium acetate-0.1% formic acid.

When the detection is performed with a 2 mM aqueous solution of ammonium acetate-0.1% formic acid as a mobile phase A and with 2 mM methanol solution of ammonium acetate-0.1% formic acid as a mobile phase B, the sensitivity is high; when 50 µL whole blood is used, the minimum concentration point (S1) of the standard curves of the four immunosuppressors completely satisfies the minimum quantitative requirements.

On the other hand, the present invention provides a method for detecting immunosuppressors in whole blood, the detection is performed by using the above detection kit, comprising system suitability test, sample preparation, sample pretreatment and sample detection, where the sample pretreatment includes the following steps: taking the internal standard solution and internal standard diluent for mixing according to a ratio of 1:24 to obtain an internal standard working solution; taking a sample and the internal standard working solution for mixing evenly according to a ratio of 1:3-1:7, and performing centrifugation, then taking supernatant for detection by high performance liquid chromatography-tandem mass spectrometry.

Further, during the sample detection, isotopically-labeled sirolimus serves as an internal standard of everolimus, thus detecting a content of everolimus.

Further, during the sample pretreatment, a volume ratio of the sample to the internal standard solution is 1:5.

Further, the sample pretreatment includes the following steps: taking the internal standard solution and internal standard diluent for mixing according to a ratio of 1:24 to obtain an internal standard working solution; taking and adding 50 µL sample to a 96-well plate or a centrifugal tube; adding 250 µL internal standard working solution for vortex mixing for 5 min; after standing for 5 min at room temperature, vortex mixing for 5 min again; centrifuging for 10 min at a revolving speed of 4000 rpm, then taking supernatant for detection by high performance liquid chromatography-tandem mass spectrometry.

The system suitability test is performed before sample detection, the system suitability solution is directly fed for 3 times and detected by high performance liquid chromatography-tandem mass spectrometry to judge whether the high performance liquid chromatography-tandem mass spectrometry system is normal through the dwell time, response strength and precision of the target substance.

The detection method provided by the present invention has a small amount of sample, only 50 µL, thus reducing the difficulty of blood sampling clinically.

Further, the sample detection includes liquid chromatography and tandem mass spectrometry; gradient elution is used; and the tandem mass spectrum: electrospray ionization (ESI) ion source and positive ion Multiple Reaction Monitoring (MRM) Mode.

Further, the gradient elution time is 2 min and the gradient elution procedure is as follows:

| Time (min) | Mobile phase A % | Mobile phase B % | Flow rate (ml/min) |
|---|---|---|---|
| 0.00 | 80 | 20 | 0.5 |
| 0.2 | 80 | 20 | 0.5 |
| 1 | 2 | 98 | 0.5 |
| 1.6 | 2 | 98 | 0.5 |
| 2.0 | 80 | 20 | 0.5 |

The above elution conditions are used to eliminate the interference of the whole blood matrix on the detection of the four immunosuppressors, thus ensuring the detection accuracy. The whole detection time is short and lasts 2 min, thus shortening the sample detection time. A specific gradient elution procedure is used for gradient elution to ensure the sample separation effect. Mass spectrometry simultaneously achieves the accurate detection of the four immunosuppressors, which greatly shortens the detection time of a single sample, effectively reduces the analysis cost. Moreover, the method of the present invention has a wide reportable range, capable of accurately analyzing the whole blood samples at different blood concentration levels.

Further, the high performance liquid chromatography conditions are as follows: the chromatographic column is a C18 chromatographic column, the mobile phase has a flow rate of 0.5 mL/min and column temperature is 55° C.

Further, the mass spectrometry conditions are as follows:

| Ionization mode | Electrospray ionization ion source (ESI+) | Scan Mode | Multiple Reaction Monitoring (MRM) Mode |
|---|---|---|---|
| Curtain gas | 20 L/min | Temperature (TEM) | 400° C. |
| Collision gas | 6 L/min | | |

Further, the mass spectrometry conditions are as follows: the four immunosuppressors for detection and a mass-to-charge ratio (m/z) of parent ion/daughter ion pair of the internal standards are shown in the table below:

| Analyte/internal standard | Q1 | Q3 |
|---|---|---|
| Tacrolimus | 821.0 | 768.5 |
|  | 821.0 | 786.4 |
| Cyclosporine A | 602.1 | 100.2 |
|  | 602.1 | 156.2 |
| Everolimus | 975.3 | 908.5 |
|  | 975.3 | 926.5 |
| Sirolimus | 931.3 | 864.5 |
|  | 931.3 | 882.6 |
| Tacrolimus-13C-d4 | 826.3 | 773.5 |
|  | 826.3 | 791.5 |
| Cyclosporine-d4 | 604.1 | 100.3 |
|  | 604.1 | 156.1 |
| Sirolimus-d3 | 934.5 | 864.6 |
|  | 934.5 | 882.5 |

Further, the method further includes data analysis, and major steps are as follows: drawing a standard curve and calculating concentrations of the immunosuppressors in human whole blood sample to be detected.

In a further aspect, the prevent invention provides use of vitamin E in the preparation of a stabilizer of an immunosuppressor solution, and the immunosuppressor is one or more of cyclosporine A, tacrolimus, sirolimus and everolimus.

The prevent invention has the following beneficial effects:
(1) an internal standard solution is added with an antioxidant, vitamin E, and mixed with an internal standard diluent containing zinc sulfate heptahydrate, purified water and methanol for sample pretreatment, which not only exerts the function of the internal standard, but also synchronously achieves erythrocyte treatment, protein precipitation and target substance extraction. Moreover, the present invention enables the immunosuppressor to be more stable in a solution matrix, thus promoting the detection accuracy and sensitivity;
(2) vitamin E is added to the internal standard solution and the system suitability solution; and acetonitrile serves as a solvent, such that the internal standard solution and the system suitability solution are very stable, and can be stored for a long time with a service life of two years above, and used at any time if necessary; therefore, the detection process is more simple and efficient, detection cost is lower, and the detection result is more accurate and stable.
(3) isotopically-labeled sirolimus serves as an internal standard of everolimus to substitute isotopically-labeled everolimus, thus overcoming the interference of everolimus on isotopically-labeled everolimus and satisfying the detection requirements, reducing the cost of the internal standard; therefore, the present invention has a lower detection cost, more accurate and stable detection results.

DETAILED DESCRIPTION OF THE EMBODIMENTS

Figure 1A:
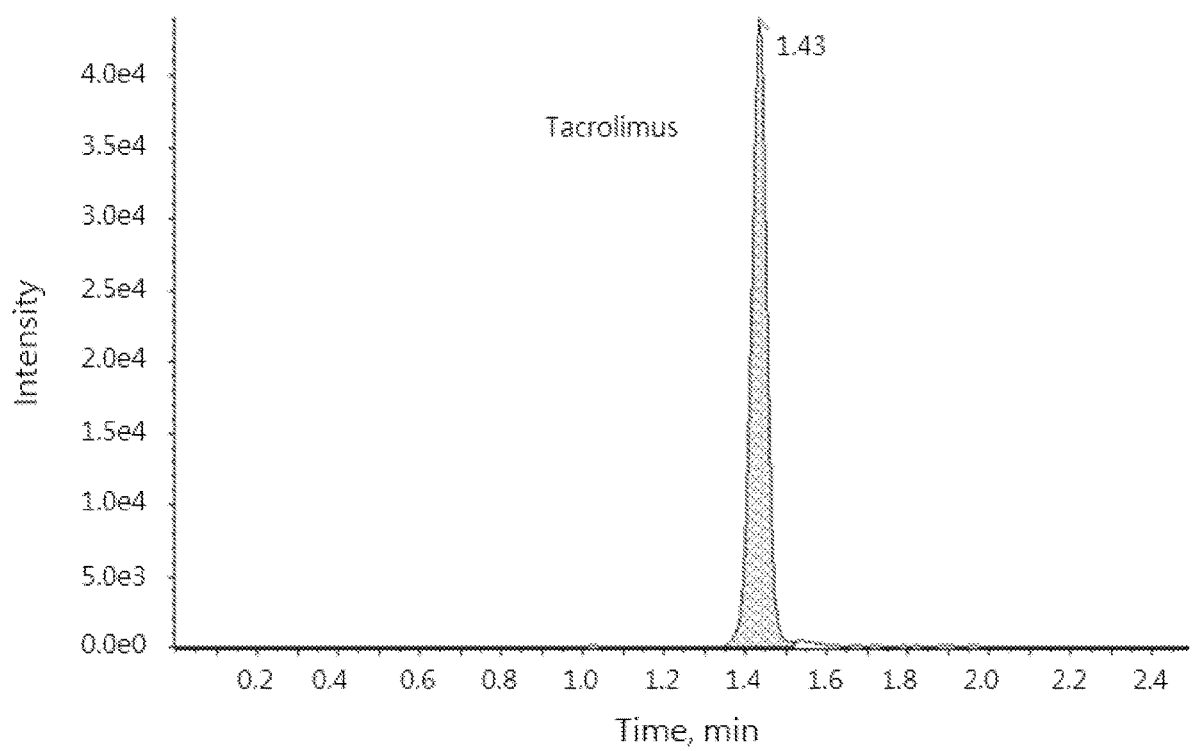
FIG. 1A-FIG. 1D are a chromatogram of a standard curve S1 in Example 1.

The present invention will be further described in detail with reference to the drawings and examples. It should be indicated that the examples below aim at facilitating the understanding of the present invention, but not limiting the present invention.

Example 1 Sample Preparation, Pretreatment and Detection

I. Sample Preparation
1. Preparation of a Standard Curve and a Quality Control Sample Standard substances of immunosuppressors cyclosporine A, tacrolimus, sirolimus and everolimus were prepared into a mixed solution as a stock solution of a standard working solution and a quality control working solution; sterile bovine blood containing a matrix additive of 1.0 mg/mL vitamin E was used as a matrix for preparation, thus preparing a standard curve and a quality control sample.

4 immunosuppressors had 10 series concentrations (S1-S10) in the standard substance, as shown in Table 1:

TABLE 1

10 series concentrations (S1-S10) of the 4 immunosuppressors in the standard substance

| ng/ml | Cyclosporine A | Tacrolimus | Sirolimus | Everolimus |
|---|---|---|---|---|
| S1 | 10 | 1 | 1 | 1 |
| S2 | 15 | 1.5 | 1.5 | 1.5 |
| S3 | 25 | 2.5 | 2.5 | 2.5 |
| S4 | 50 | 5 | 5 | 5 |
| S5 | 75 | 7.5 | 7.5 | 7.5 |
| S6 | 100 | 10 | 10 | 10 |
| S7 | 250 | 25 | 25 | 25 |
| S8 | 500 | 50 | 50 | 50 |
| S9 | 750 | 75 | 75 | 75 |
| S10 | 1000 | 100 | 100 | 100 |

4 immunosuppressors had 3 series concentrations at low (L), medium (M) and high (H) levels in the quality control substance, as shown in Table 2:

TABLE 2

Three series concentrations of the 4 immunosuppressors in the quality control substance

| ng/ml | Cyclosporine A | Tacrolimu | Sirolimus | Everolimus |
|---|---|---|---|---|
| L | 30 | 3 | 3 | 3 |
| M | 300 | 30 | 30 | 30 |
| H | 800 | 80 | 80 | 80 |

2. Preparation of an Internal Standard Solution and an Internal Standard Diluent
(1) Preparation of an Internal Standard Solution A mixed internal standard working solution was prepared, and concentrations of cyclosporine A-d4, tacrolimus-13C-d4, and sirolimus-d3 were respectively 1 μg/mL, 50 ng/mL and 50 ng/mL; and an additive 1.0 mg/mL vitamin E was added, acetonitrile served as a solvent, and mixed into an internal standard solution.

(2) Preparation of an Internal Standard Diluent 17.8 g zinc sulfate heptahydrate, 300 ml purified water and 700 ml methanol were respectively weighed and prepared into an internal standard diluent.

3. Preparation of a System Suitability Solution

20 μL of the mixed internal standard solution containing 100 μg/mL cyclosporine A-d4, 5 μg/mL tacrolimus-13C-d4 and 5 μg/mL sirolimus-d3, 100 μL of the mixed standard solution containing 8 μg/mL cyclosporine A, 0.8 μg/mL tacrolimus, 0.8 μg/mL sirolimus and 0.8 μg/mL everolimus, and 59.88 mL of acetonitrile solution containing 1.0 mg/mL VE were respectively taken and mixed into a system suitability solution.

II. Sample Pretreatment (1) The internal standard solution and internal standard diluent were taken and mixed evenly according to a ratio of 1:24 to obtain an internal standard working solution;

(2) 50 μL sample was taken and added to a 96-well plate or a centrifugal tube;

(3) 250 μL internal standard working solution was added for vortex mixing for 5 min, subjected to standing for 5 min at room temperature, then vortex mixed for 5 min, and centrifuged for 10 min at a revolving speed of 4000 rpm, then supernatant was taken for further detection.

III. Sample Detection

Figure 1B:
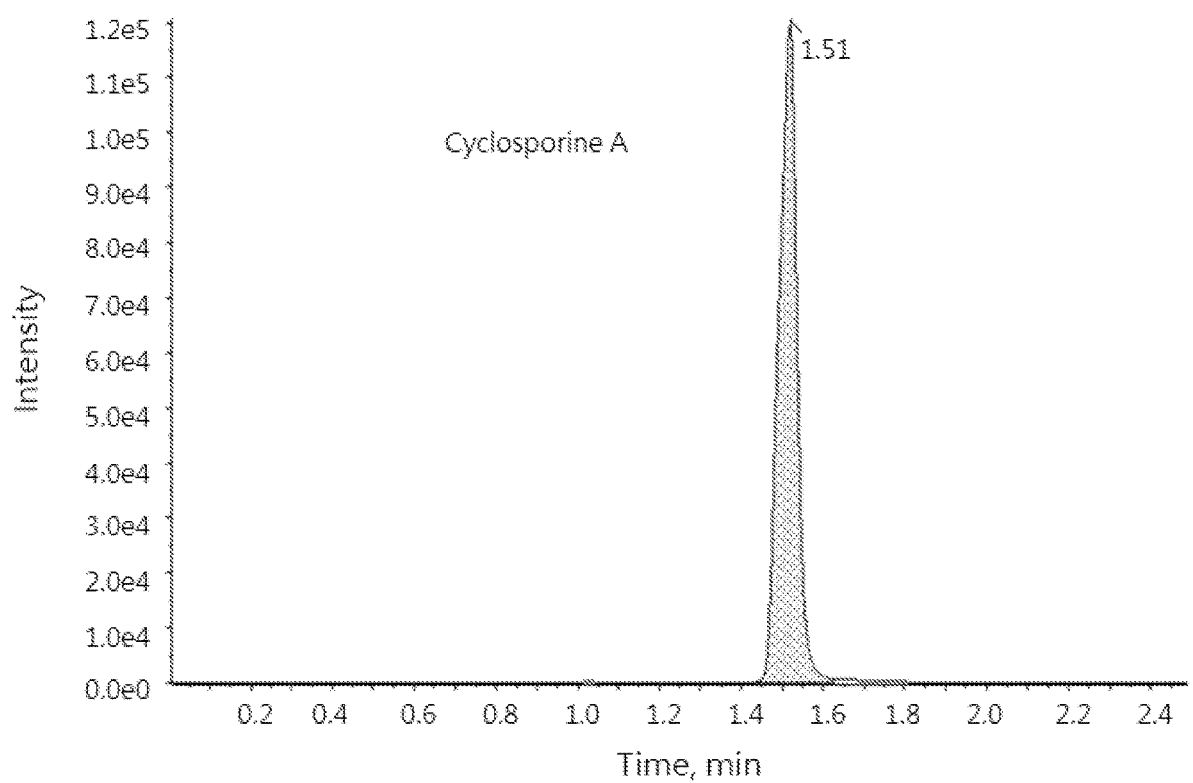
Figure 1C:
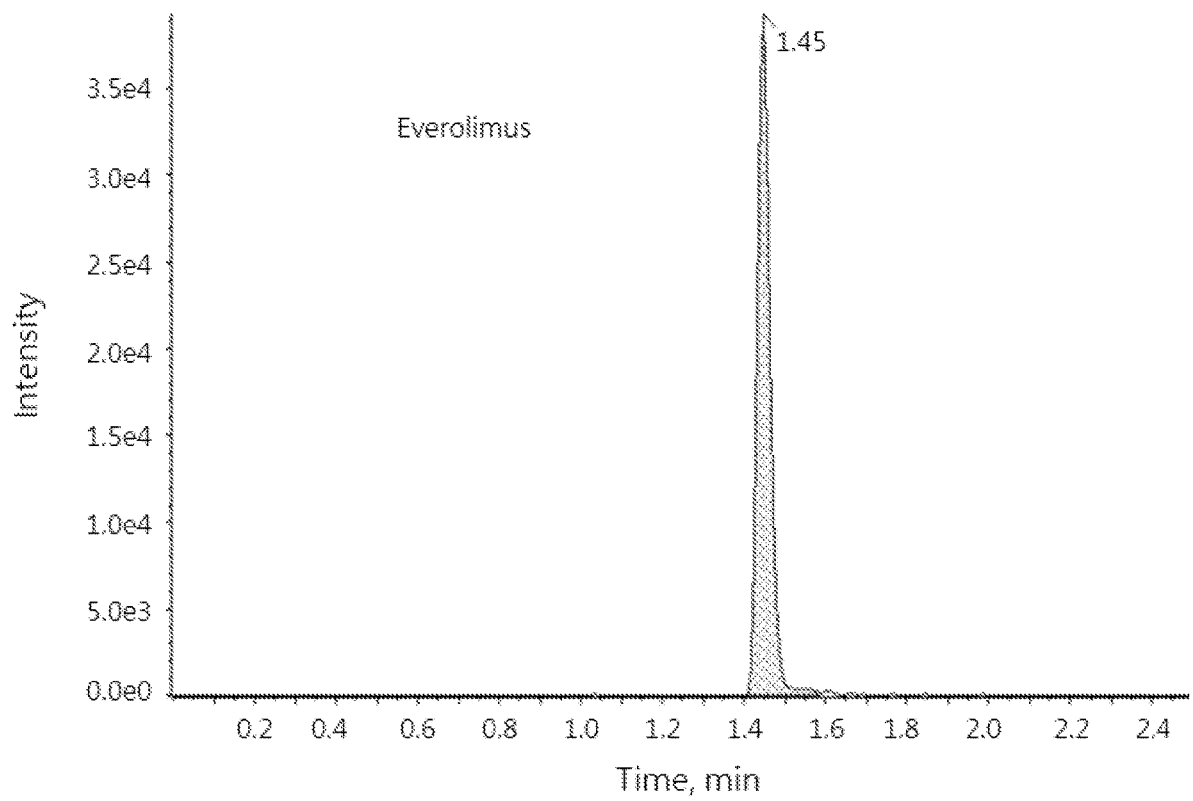
Figure 1D:
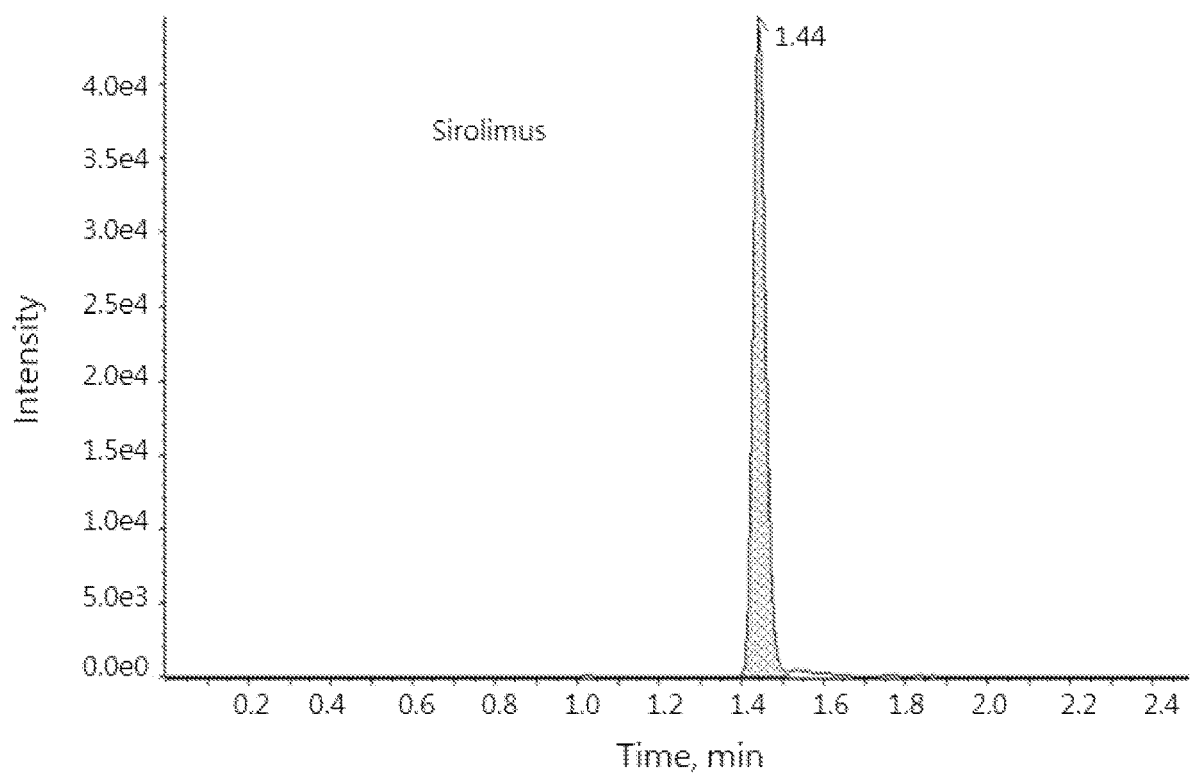

Supernatant was taken and detected by high performance liquid chromatography-tandem mass spectrometry; and a spectrogram of the standard curve at the lowest point was shown in FIG. 1. Specific analysis conditions were as follows: gradient elution was used to an instrumental method; and the tandem mass spectrum: electrospray ionization (ESI) ion source and positive ion Multiple Reaction Monitoring (MRM) Mode were taken. The chromatographic column was a C18 chromatographic column, the mobile phase had a flow rate of 0.5 mL/min and column temperature was 55° C., and the gradient elution procedure was as follows:

| Time (min) | Mobile phase A % | Mobile phase B % | Flow rate (ml/min) |
|---|---|---|---|
| 0.00 | 80 | 20 | 0.5 |
| 0.2 | 80 | 20 | 0.5 |
| 1 | 2 | 98 | 0.5 |
| 1.6 | 2 | 98 | 0.5 |
| 2.0 | 80 | 20 | 0.5 |

The mass spectrometry conditions were as follows:

| Ionization mode | Electrospray ionization ion source (ESI+) | Scan Mode | Multiple Reaction Monitoring (MRM) Mode |
|---|---|---|---|
| Curtain gas | 20 L/min | Temperature (TEM) | 400° C. |
| Collision gas | 6 L/min | | |

Four immunosuppressors for detection and a mass-to-charge ratio (m/z) of parent ion/daughter ion pair of the internal standards were shown in the table below:

| Analyte/internal standard | Q1 | Q3 |
|---|---|---|
| Tacrolimus | 821.0 | 768.5 |
| | 821.0 | 786.4 |
| Cyclosporine A | 602.1 | 100.2 |
| | 602.1 | 156.2 |
| Everolimus | 975.3 | 908.5 |
| | 975.3 | 926.5 |
| Sirolimus | 931.3 | 864.5 |
| | 931.3 | 882.6 |
| Tacrolimus-13C-d4 | 826.3 | 773.5 |
| | 826.3 | 791.5 |

| Analyte/internal standard | Q1 | Q3 |
|---|---|---|
| Cyclosporine-d4 | 604.1 | 100.3 |
| | 604.1 | 156.1 |
| Sirolimus-d3 | 934.5 | 864.6 |
| | 934.5 | 882.5 |

The detection of the 4 immunosuppressors could be determined through the ion pair detected by selective reaction monitoring and the corresponding dwell time; and quantification could be performed through the internal standard of each immunosuppressor.

After the sample was separated by liquid chromatography, different immunosuppressor appeared peaks at different elution time, and were detected by mass spectrometry MRM, thus detecting the content. According to the series concentrations of the standard sample S1, sterile bovine blood containing an additive 1.0 mg/mL vitamin E served as a matrix to prepare a sample to be detected for detection, and the detection spectrogram was shown in FIG. 1. As shown in FIG. 1, the 4 immunosuppressors could be detected simultaneously and accurately according to the method provided by the example.

Example 2 Influence of Adding an Antioxidant on the Stability of the Immunosuppressors In this example, according to the method provided in Example 1, different kinds of antioxidants were respectively used and prepared into an internal standard solution and a system suitability solution having the same concentration; then the solution was put for 14 d at 37° C. to survey the influences of different antioxidants on the service life of cyclosporine-d4, tacrolimus-13C-d4, sirolimus-d3 contained in the internal standard solution and the cyclosporine A, tacrolimus, sirolimus, and everolimus contained in the system suitability solution. Antioxidants included 2,6-di-tert-butyl-p-cresol, vitamin E, vitamin C, β-carotene, and sodium metabisulfite. The results were shown in Tables 1 and 2:

TABLE 1

Influences of the different antioxidants on the 14 d stability of cyclosporine A, tacrolimus, sirolimus, and everolimus contained in the system suitability solution at 37° C.:

| Antioxidant | Peak area of system suitability solution | | | |
|---|---|---|---|---|
| | Cyclosporine A | Tacrolimus | Sirolimus | Everolimus |
| Initial values | 209326 | 74430 | 115492 | 111146 |
| Free of adding antioxidant | 216288 | 7408 | 4216 | 2401 |
| 2,6-di-tert-butyl-p-cresol | 214654 | 27771 | 5499 | 3533 |
| Vitamin E | 221593 | 69879 | 98087 | 98290 |
| Vitamin C | 210444 | 30470 | 5167 | 11782 |
| β-carotene | 198460 | 8659 | 8219 | 3599 |
| Sodium metabisulfite | 222696 | 8044 | 7075 | 6256 |

TABLE 2

Influences of the different antioxidants on the 14 d stability of cyclosporine-d4, tacrolimus-13C-d4, sirolimus-d3, and everolimus-d4 contained in the internal standard solution at 37° C.:

| Antioxidant | Peak area of internal standard solution | | |
|---|---|---|---|
| | CyclosporineA-d4 | Tacrolimus-13C-d4 | Sirolimus-d3 |
| Initial values | 140935 | 60178 | 71424 |
| Free of adding antioxidant | 129898 | 6069 | 3768 |
| 2,6-di-tert-butyl-p-cresol | 136211 | 28579 | 7033 |
| Vitamin E | 143337 | 53397 | 62889 |
| Vitamin C | 147298 | 25618 | 6664 |
| P-carotene | 147555 | 5494 | 3308 |
| Sodium metabisulfite | 139515 | 5764 | 5301 |

It can be seen both in Tables 1 and 2 that in case of not adding an antioxidant, and after the solutions were put for 14 d at 37° C., the content of the immunosuppressors in the system suitability solution and isotopically-labeled immunosuppressors in the internal standard solution significantly decreased, especially, the content of tacrolimus, everolimus and sirolimus almost dropped dramatically, indicating that the 4 immunosuppressors or isotope internal standards thereof in the system suitability solution and the internal standard solution were rather unstable.

The addition of different antioxidants had different influences on the stability of the 4 immunosuppressors or isotope internal standards thereof in the system suitability solution and the internal standard solution. Experimental results showed that the addition of vitamin E can obviously improve the stability of the four immunosuppressors, after the solution was put for 14 d at 37° C., the 4 immunosuppressors or isotope internal standards thereof in the system suitability solution and the internal standard solution had a content change within 15%, and had better stability.

Through further experiments, the example further verified that after being put for 2 years at 2-8° C., the 4 immunosuppressors or isotope internal standards thereof in the system suitability solution and the internal standard solution added with vitamin E still kept a stable content.

Example 3 Selection for the Content of Vitamin E

In this example, according to the method provided in Example 1, standard solutions of cyclosporine A, tacrolimus, sirolimus, and everolimus were added to sterile bovine blood, and vitamin E at different concentrations was added, then the remaining solution was put for 14 d at 37° C. to survey the influences of the vitamin E at different concentrations on the service life of cyclosporine A, tacrolimus, sirolimus, and everolimus in whole blood. The results were shown in Table 3:

TABLE 3

Influences of the vitamin E content on the detection results of the sample after being put for 14 d at 37° C.:

| Concentration of vitamin E | Sample detection concentration (ng/mL) | | | |
|---|---|---|---|---|
| | Cyclosporine A | Tacrolimus | Sirolimus | Everolimus |
| Initial values | 786.5 | 79.7 | 76.3 | 80.1 |
| 0.5 mg/mL | 801.2 | 73.3 | 72.2 | 62.1 |

TABLE 3-continued

Influences of the vitamin E content on the detection results of the sample after being put for 14 d at 37° C.:

| Concentration of vitamin E | Sample detection concentration (ng/mL) | | | |
|---|---|---|---|---|
| | Cyclosporine A | Tacrolimus | Sirolimus | Everolimus |
| 1.0 mg/mL | 758.5 | 80.1 | 75.7 | 75.3 |
| 1.5 mg/mL | 775.2 | 79.0 | 75.4 | 75.7 |

It can be seen from Table 3 that when the concentration of vitamin E was 0.5 mg/mL, after the solution was put for 14 d at 37° C., the concentration of everolimus decreased by 22.5%, not being up to the requirement; and when the concentration of vitamin E was 1.0 mg/mL and 1.5 mg/mL, cyclosporine A, tacrolimus, sirolimus, and everolimus had no obvious decline; therefore, vitamin E had a preferred concentration of 1.0 mg/mL.

Example 4 Interference of Everolimus on Everolimus Isotopes

1. Detection Results of Everolimus Standards

In the example, according to the method provided by Example 1, a standard solution of everolimus was taken for detection by high performance liquid chromatography-tandem mass spectrometry; and the detection results were shown in Table 4.

Example 4 Interference of Everolimus on an Internal Standard of Everolimus-d4

| Test results of everolimus standards | Peak area of everolimus | Peak area of everolimus-d4 channel |
|---|---|---|
| | 1373689 | 15205 |

It can be seen from Table 4 that no everolimus-d4 was added to the everolimus standard solution, but a signal was found in the everolimus-d4 channel in the detection result, indicating that everolimus would disturb everolimus isotopes. Therefore, if everolimus isotopes were used as internal standards for detection, the detection result would be influenced due to the existing interference, such that the accuracy of everolimus would be seriously affected.

2. Detection Results of Everolimus Standard Solutions at Different Concentrations Clinical samples were taken and respectively added with everolimus standard solutions at different concentrations; and everolimus-d4 served as an internal standard to detect the recovery rate of the sample after adding the internal standard; 6 samples were set in parallel, and the results were shown in Table 5.

5. Detection results of everolimus standard solutions at different concentrations

| Sample | Adding amount of everolimus (ng/mL) | | |
|---|---|---|---|
| | 4 | 16 | 50 |
| 1 | 3.95 | 14.23 | 39.72 |
| 2 | 3.48 | 13.37 | 39.84 |
| 3 | 3.82 | 13.90 | 40.45 |
| 4 | 3.87 | 14.04 | 38.60 |

5. Detection results of everolimus standard solutions at different concentrations

| | Adding amount of everolimus (ng/mL) | | |
|---|---|---|---|
| Sample | 4 | 16 | 50 |
| 5 | 3.98 | 13.61 | 37.68 |
| 6 | 3.97 | 13.59 | 38.69 |
| Mean value | 3.85 | 13.79 | 39.17 |
| CV | 4.9% | 2.32% | 2.59% |
| Recovery rate | 96.1% | 86.18% | 78.34% |

It can be seen from Table 5 that in everolimus standards at different concentrations, when everolimus-d4 served as an internal standard for detection, with the increase of the everolimus concentration, the detected recovery rate of everolimus became lower and lower; and when the adding amount was up to 50 ng/mL, the recovery rate was lower than 85%, which completely could not satisfy the accuracy requirements. Therefore, the addition of everolimus-d4 as an internal standard would seriously influence the detection accuracy of the everolimus content.

Sirolimus and everolimus have a very similar structure. A large number of experiments (data omitted) proved that an isotope internal standard of sirolimus served as an internal standard of everolimus, which completely could satisfy the detection requirements of everolimus, and could reduce the cost of the internal standard, and further promote the accuracy and sensitivity of the detection result.

Example 5 Clinical Verification Experiment

Clinical samples were taken and respectively added with standard solutions of cyclosporine A, tacrolimus, sirolimus, and everolimus to prepare into recovery rate samples at high, medium, and low levels of concentrations for detection according to the method provided in Example 1; 6 samples were taken in parallel for pretreatment, then the recovery rate was calculated. Recovery rate results were shown in Table 6:

TABLE 6

Results of clinical verification experiment

| Recovery rate sample | | Tacrolimus | Cyclosporine | Everolimus | Sirolimus |
|---|---|---|---|---|---|
| LQC | Adding amount (ng/mL) | 4 | 40 | 4 | 4 |
| | Sample 1 | 3.88 | 39.08 | 3.95 | 3.37 |
| | Sample 2 | 3.44 | 39.31 | 3.48 | 3.92 |
| | Sample 3 | 3.77 | 41.04 | 3.82 | 3.6 |
| | Sample 4 | 4.03 | 38.09 | 3.87 | 3.87 |
| | Sample 5 | 3.59 | 38.36 | 3.98 | 4.05 |
| | Sample 6 | 3.8 | 39.75 | 3.97 | 3.76 |
| | Mean value (ng/mL) | 3.75 | 39.27 | 3.85 | 3.76 |
| | CV | 5.6% | 2.7% | 4.9% | 6.5% |
| | Recovery rate | 93.8% | 98.2% | 96.1% | 94.0% |
| MQC | Adding amount (ng/mL) | 16 | 160 | 16 | 16 |
| | Sample 1 | 15.87 | 167.63 | 15.65 | 14.01 |
| | Sample 2 | 16.19 | 163.29 | 14.71 | 13.92 |
| | Sample 3 | 13.75 | 168.83 | 15.29 | 14.81 |
| | Sample 4 | 15.52 | 163.54 | 15.44 | 13.63 |
| | Sample 5 | 15.67 | 164.38 | 14.97 | 14.41 |
| | Sample 6 | 13.93 | 165.45 | 14.95 | 14.7 |
| | Mean value (ng/mL) | 15.16 | 165.52 | 15.17 | 14.25 |
| | CV | 6.9% | 1.4% | 2.3% | 3.3% |
| | Recovery rate | 94.7% | 103.5% | 94.8% | 89.0% |
| HQC | Adding amount (ng/mL) | 50 | 500 | 50 | 50 |
| | Sample 1 | 47.02 | 495.22 | 44.88 | 50.27 |
| | Sample 2 | 49.23 | 489.83 | 45.02 | 47.67 |
| | Sample 3 | 51.89 | 494.37 | 45.71 | 46.66 |
| | Sample 4 | 46.92 | 503.76 | 43.62 | 46.2 |
| | Sample 5 | 47.42 | 495.44 | 42.58 | 50.65 |
| | Sample 6 | 49.22 | 501.16 | 43.72 | 45.36 |
| | Mean value (ng/mL) | 48.62 | 496.63 | 44.26 | 47.80 |
| | CV | 3.9% | 1.0% | 2.6% | 4.6% |
| | Recovery rate | 97.2% | 99.3% | 88.5% | 95.6% |

To summarize the above data, we have surveyed the accuracy and recovery rate of the 4 immunosuppressors at three (high, medium, and low) quality control levels; and the results indicate that the accuracy of the method is less than 7%, and the recovery rate is basically 90% above, indicating that the method accords with the clinical detection requirements.

Even though the present invention is disclosed above, but it is not limited thereto. A person skilled in the art can make various alterations and modifications within the spirit and scope of the present invention. Therefore, the protection scope of the present invention should be subjected to the scope defined by the claims.

The invention claimed is:

1. A method for detecting an immunosuppressor in whole blood, comprising the steps:
   providing a detection kit comprising:
      an internal standard solution, wherein the internal standard solution comprises an additive, and the additive is one or more of 2,6-di-tert-butyl-p-cresol, vitamin E, vitamin C, β-carotene, and sodium metabisulfite;
   performing a system suitability test, preparing a sample, pre-treating the sample and detecting the sample;
   wherein the sample pretreatment comprises the following steps:
      taking the internal standard solution and internal standard diluent from the detection kit for mixing according to a ratio of 1:24 to obtain an internal standard working solution;
      taking a sample and the internal standard working solution for mixing evenly according to a ratio of 1:3-1:7, and performing centrifugation, then taking supernatant for detection by high performance liquid chromatography-tandem mass spectrometry.

2. The method of claim 1, wherein during the sample pretreatment, a volume ratio of the sample to the internal standard solution is 1:5.

3. The method of claim 2, wherein during the sample detection, isotopically-labeled sirolimus serves as an internal standard of everolimus, thus detecting a content of everolimus.

4. The method of claim 3, wherein gradient elution is used in the detection by high performance liquid chromatography-tandem mass spectrometry, and the gradient elution time is 2 min, and the gradient elution procedure is as follows:

| Time (min) | Mobile phase A % | Mobile phase B % | Flowrate (ml/min) |
|---|---|---|---|
| 0.00 | 80 | 20 | 0.5 |
| 0.2 | 80 | 20 | 0.5 |
| 1 | 2 | 98 | 0.5 |
| 1.6 | 2 | 98 | 0.5 |
| 2.0 | 80 | 20 | 0.5. |

5. The method of claim 1, wherein the additive in the detection kit is vitamin E.

6. The method of claim 5, wherein the vitamin E has a concentration of 0.5-1.5 mg/mL.

7. The method of claim 6, wherein the vitamin E has a concentration of 1.0 mg/mL.

8. The method of claim 7, wherein the immunosuppressor is one or more of cyclosporine A, tacrolimus, sirolimus and everolimus.

9. The method of claim 8, wherein the internal standard solution further comprises an immunosuppressor internal standard and acetonitrile, and the acetonitrile is a solvent of the internal standard solution.

10. The method of claim 9, wherein the immunosuppressor is an isotopically-labeled immunosuppressor, wherein an internal standard of cyclosporine A is isotopically-labeled cyclosporine A, an internal standard of tacrolimus is isotopically-labeled tacrolimus, and internal standards of sirolimus and everolimus are isotopically-labeled sirolimus.

11. The method of claim 1, wherein the detection kit further comprises an internal standard diluent, and the internal standard diluent comprises zinc sulfate heptahydrate, purified water and methanol.

12. The method of claim 11, wherein in the internal standard diluent, a volume ratio of purified water to methanol is 3:7, and zinc sulfate heptahydrate has a content of 60 mM.

13. The method of claim 12, wherein a volume ratio of the internal standard solution and the internal standard diluent is 1:24.

14. The method of claim 13, wherein the detection kit further comprises a system suitability solution, wherein the system suitability solution comprises one or more of cyclosporine A, tacrolimus, sirolimus, and everolimus, as well as one or more of isotopically-labeled cyclosporine A, tacrolimus and sirolimus, and further comprises a solvent and an additive; the solvent is additive-containing acetonitrile; and the additive is any one or more of 2,6-di-tert-butyl-p-cresol, vitamin E, vitamin C, β-carotene, and sodium metabisulfite.

15. The method of claim 14, wherein the additive of the system suitability solution is vitamin E having a concentration of 0.5-1.5 mg/mL.

16. The method of claim 15, wherein the detection kit further comprises a standard sample and a quality control sample; the standard sample and the quality control sample are prepared by using a sterile bovine blood containing a matrix additive as a matrix; the matrix additive comprises vitamin E; the standard sample is a sample comprising any one of more of cyclosporine A, tacrolimus, sirolimus and everolimus at a standard concentration; and the quality control sample is a sample comprising three different levels (low, medium and high) of concentrations.

17. The method of claim 16, wherein the vitamin E in the matrix addictive has a concentration of 0.5-1.5 mg/mL.

18. The method of claim 17, wherein the detection kit further comprises a mobile phase of liquid chromatography (LC); the mobile phase of LC comprises a mobile phase A and a mobile phase B; the mobile phase A is a 2 mM aqueous solution of ammonium acetate-0.1% formic acid; and the mobile phase B is 2 mM methanol solution of ammonium acetate-0.1% formic acid.

* * * * *